United States Patent [19]

Christians et al.

[11] Patent Number: 5,290,757
[45] Date of Patent: Mar. 1, 1994

US005290757A

[54] PREEMERGENCE WEED CONTROL USING DIPEPTIDES FROM CORN GLUTEN HYDROLYSATE

[75] Inventors: Nick E. Christians, Ames; John T. Garbutt, Muscatine; Dianna Liu, Ames, all of Iowa

[73] Assignees: Iowa State University Research Foundation, Inc., Ames; Grain Processing Corporation, Muscatine, both of Iowa

[21] Appl. No.: 101,577

[22] Filed: Aug. 3, 1993

[51] Int. Cl.⁵ ............................................. A01N 37/30
[52] U.S. Cl. ..................................... 504/335; 504/339
[58] Field of Search ............................... 504/335, 339; A01N 37/30

[56] References Cited

U.S. PATENT DOCUMENTS

| | | | |
|---|---|---|---|
| 3,161,497 | 12/1964 | Amburn | 504/116 |
| 4,734,120 | 3/1988 | Kehne et al. | 504/205 |
| 4,929,270 | 5/1990 | Cardellina, II et al. | 504/235 |
| 5,030,268 | 7/1991 | Christians | 504/116 |

Primary Examiner—Glennon H. Hollrah
Assistant Examiner—S. Mark Clardy
Attorney, Agent, or Firm—Merchant, Gould, Smith, Edell, Welter & Schmidt

[57] ABSTRACT

A composition useful as a selective preemergence herbicide is provided, comprising an effective amount of a dipeptide selected from the group consisting of Gln-Gln, Ala-Asn, Ala-Gln, Gly-Ala, Ala-Ala and mixtures thereof, in combination with a compatible carrier vehicle.

19 Claims, No Drawings

PREEMERGENCE WEED CONTROL USING DIPEPTIDES FROM CORN GLUTEN HYDROLYSATE

BACKGROUND OF THE INVENTION

Herbicides have been widely employed to destroy unwanted plants or "weeds", to prevent their growth on bare ground or in established crops, and to promote the growth of desirable plants, such as grains, fruits and vegetables. In fact, millions of pounds of herbicide are applied directly to the soil on an annual basis. In general, herbicides consist of two types, non-selective and selective. Non-selective herbicides kill all plant life on the plot of soil on which they are applied. Selective herbicides, on the other hand, kill or inhibit the establishment of certain types of plant life, such as weeds, while leaving the desirable, surrounding crops on which they are applied relatively undamaged. Examples of selective herbicides include phenolics, carbamates, and dinitroanilines.

One way to selectively eliminate unwanted plants without injuring surrounding plant life is to inhibit germination or establishment of the seeds of the unwanted plants. In order to accomplish this, a herbicide must be applied before the unwanted plants emerge from the soil, either to a bare plot of soil into which established plants will be transplanted, or to a plot of soil comprising an established stand of desirable plants, but relatively few weeds. Such herbicides are often referred to as preemergence herbicides.

While various types of herbicides exist, most of them are based on synthetic chemical toxins. As a result of their toxic nature, they are undesirable for many applications. This is particularly a problem when these materials come in contact with the public as is the case in turfgrass areas and in the production of food crops consumed by humans. While synthetic chemical herbicides may effectively destroy unwanted plant life, they may contaminate the soil and the crops themselves. They may also contaminate the ground water as a result of run off or erosion.

The disadvantages of synthetic chemical herbicides have become more visible as a result of heightened public awareness and concern for environmental protection and consumer safety. This in turn has led to the search for non-toxic, natural herbicides which can provide a greater margin of safety for the public and for the environment. In the area of herbicides or insecticides, however, few effective materials derived from naturally-occurring sources are known. *Bacillus thurigiensis* (Bt toxins), *Bacillus popilliae, Serratia eritomophila, Puccinia chondrillina*, and *Sclerotinia sclerotiotum* represent some examples of natural herbicides and insecticides that currently exist.

Corn gluten meal is capable of inhibiting root growth of germinating plants, while no damage is observed to plants that have formed a mature root system. Christians (U.S. Pat. No. 5,030,268) discloses that this material is useful as a natural preemergence herbicide for various plant production systems, including turfgrass areas, where it acts to inhibit the establishment of annual weeds, such as crabgrass (*Digitaria spp.*).

Corn gluten meal, however, is essentially water-insoluble. This characteristic limits its use as an herbicide for some applications. Since corn gluten meal is insoluble and cannot be dissolved and sprayed, it is difficult to apply evenly. As a result, there is a risk that the soil on which it is applied will not be completely covered, thereby significantly reducing its effectiveness. Also, sprayable herbicides are advantageous for application to certain crops.

The effectiveness of a herbicide also depends upon its ability to permeate the soil. Water-insoluble or slightly soluble materials do not permeate the soil as well as do water-soluble materials. Factors such as wind or drought can further reduce the availability of such materials.

Therefore, a continuing need exists for potent, natural preemergence herbicides which are also highly water dispersible and/or water soluble.

SUMMARY OF THE INVENTION

During studies designed to isolate and identify one or more active components of corn gluten, we unexpectedly found that hydrolyzed protein from corn gluten provided an effective water-soluble, preemergence herbicide that is much more active than the corn gluten meal itself. Furthermore, investigation of these hydrolysates led to the isolation and identification of five dipeptides which are highly effective as selective preemergence herbicides. Thus, the present invention provides a herbicidal composition comprising a dipeptide selected from the group consisting of glutaminyl-glutamine (Gln-Gln), alaninylasparagine (Ala-Asn), alaninyl-glutamine (Ala-Gln), glycinyl-alanine (Gly-Ala), alaninyl-alanine (Ala-Ala) and mixtures thereof, in combination with a compatible carrier vehicle. Compatible carrier vehicles are preferably non-toxic and include liquids such as water, used alone or in combination with non-toxic co-solvents and art-recognized surfactants, stabilizers, buffers and the like. Solid vehicles include the finely-dispersed carrier vehicles employed to deliver dust-type herbicides.

When applied to a plot of soil, either prior to planting said plot with established desirable plants, or having an established stand of desirable plants thereon, the present dipeptides inhibit the root formation of the germinating seeds of the undesirable plants or "weeds" and thus inhibit or completely block their growth and emergence. Following application of the dipeptides to the soil and planting established desirable plants in said plot, additional amounts of said dipeptides can be applied as needed, to prevent the growth of undesirable plants while not inhibiting the growth of the desirable plants, or otherwise harming them.

The present dipeptides are also effective to inhibit the emergence of a wide variety of weeds, both broadleaf and grassy, while not harming established desirable plants, both broadleaf (dicot) and grassy (monocot). Thus, the present dipeptides function as a nontoxic, selective, natural preemergence herbicides when applied at a wide variety of concentrations and intervals to the target site.

As used herein, the term "plot of soil" is intended to broadly cover volumes of solid plant support material such as the mixture of organic and inorganic materials conventionally referred to as "soil," as well as synthetic soils (or "soiless soils") and homogeneous solid supports such as beds of pebbles, sand, moss and the like. The solid plant support material may be potted, or otherwise contained, or may be a preselected portion of the ground.

The present invention also provides a two-stage chromatographic method to isolate the present dipeptides which sequentially applies gel filtration and reverse-phase HPLC to an aqueous solution of plant protein hydrolysate, i.e., corn gluten hydrolysate. The stationary phase for gel filtration preferably has an exclusion limit of less than 1500 daltons, and consists of cross-linked dextran beads such as the Sephadex resins available from Sigma Chem. Co.

The present dipeptides are identified using conventional three-letter amino acid abbreviations and are read from the amino terminus (left) to the carboxy terminus (right).

DETAILED DESCRIPTION OF THE INVENTION

The five dipeptides isolated from corn gluten meal hydrolysate that have been demonstrated to inhibit root growth of plants at the time of germination are glutaminylglutamine (Gln-Gln), alaninyl-asparagine (Ala-Asn), alaninyl-glutamine (Ala-Gln), glycinyl-alanine (Gly-Ala), and alaninyl-alanine (Ala-Ala).

Corn gluten meal is commercially available as a by-product of corn milling. It is made by drying the liquid gluten stream separated from corn during corn wet milling processing. In the wet milling process of corn, the following fractions are obtained: corn starch, corn oil, defatted corn germ, corn hulls, corn steep liquor, and corn gluten (the protein fraction). Corn gluten is typically separated from the starch stream by centrifugation to yield a thick yellow slurry of corn gluten containing 15 to 20% solids. Conventionally, corn gluten is filtered and dried to produce solid corn gluten meal, which is sold as an animal feed product. Corn gluten meal is quite insoluble in water and is typically composed of the materials listed in Table I, below.

TABLE 1

| Corn Gluten Meal Component | %, Dry Basis |
|---|---|
| Protein | 60–70 |
| Carbohydrate | 20–25 |
| Fat | 3–5 |
| Ash | 3–5 |

The present corn gluten hydrolysate is preferably prepared by a process comprising treating the corn gluten slurry with acid or with one or more enzymes. Preferably, the corn gluten is treated with one or more proteases, and most preferably, is pretreated with one or more amylases. For example, the corn gluten slurry may be treated with amylases, followed by filtration to remove the solubilized carbohydrates. The insoluble residue is then treated with one or more proteases to solubilize the protein components. After pH adjustment with acid, the slurry is filtered and/or centrifuged. The effluent is dried in a conventional manner to yield "corn gluten hydrolysate" which is essentially water soluble (>90% at 10 g/100 ml).

Alternatively, the corn gluten slurry can be treated with proteases alone and the entire reaction mixture dried, or the reaction mixture may be centrifuged or filtered and the supernatant or filtrate dried in an appropriate manner, to yield a soluble corn gluten hydrolysate.

To prepare corn gluten hydrolysates, the liquid corn gluten (15–20% solids) is preferably diluted with water to a solids concentration of about 5 to 20% and the pH adjusted to about 6.0 to 8.0, preferably to about pH 6.5. The appropriate amylase is added (0.1 to 1.0% dry basis (DB)) and the slurry jet cooked at 137° to 171° C., preferably at 160° C. for 3–4 minutes. The cooked slurry is then adjusted to about pH 4 to 5, cooled to 140° F. and, optionally, a saccharifying amylase (glucoamylase) is added (0.01 to 0.1% DB) and the slurry maintained at 140° F. for 8–16 hours, preferably about 12 hours. The slurry is then filtered and washed and the filtrate and washings discarded. The filter cake is reslurried in water to 5 to 20% solids (preferably about 7–10%) and adjusted to pH 7.5 to 9 with $Ca(OH)_2$. An alkaline protease is then added (0.1% to 1% DB) and the slurry is maintained at 50° to 60° C. for 2 to 6 hours or until the pH remains constant. The slurry is then adjusted to pH 6.0 to 6.8 (preferably pH 6.2), the precipitated $Ca_3(PO_4)_2$ and any insoluble residue is removed by filtration. The clear filtrate is then dried in an appropriate manner (i.e., spray drying, drum drying, etc.) to yield a dry solid product having greater than about 80–90% protein (Kjeldahl nitrogen $\times 6.25$), and which is essentially water-soluble at a concentration of 10% by weight.

The present dipeptides were isolated by subjecting aqueous solutions of corn gluten hydrolysate to column chromatography (gel filtration). Herbicidal fractions in the eluate were identified by their ability to inhibit the germination of seeds, such as seeds of grassy weeds, in an in vitro assay. The active fractions were further purified by reverse phase high performance liquid chromatography. The bioactive fractions were then derivatized, purified further by chromatography and the resultant peptides were sequenced to identify the peptidyl components. The bioactive dipeptides identified can be readily synthesized by methods known to the art. Peptides Ala-Ala, Ala-Asn, Ala-Gln and Gly-Ala are available from Sigma Chem. Co., St. Louis, Mo.; peptide Gln-Gln is available from Bachem Bioscience Inc.

In use, one or more of the present dipeptides are combined with an effective amount of a carrier vehicle, i.e., at about 0.25–25 wt-% of the vehicle, and applied to the target soil plot/crop by conventional means, such as spraying, watering, spreading, dusting and the like. Suitable vehicles include water or water-alcohol mixtures, optionally in combination with minor but effective amounts of surfactants, solubilization aids, stabilizers, buffers and the like. Solid carrier vehicles include those commonly employed to apply herbicides to target areas, such as ground corn cobs, clay and the like.

Preferred application rates for the herbicidal dipeptide or dipeptide mixtures at about 0.003–5 g/dm$^2$, preferably about 0.25–3.0 g/dm$^2$, of soil per application. The herbicidal composition can be simply surface-applied, or it can be mixed into the upper layer of the soil following application. The present dipeptides can also be used to augment herbicidal activity of corn gluten meal or plant protein hydrolysates.

It is believed that the present dipeptides will be effective to prevent the emergence of a wide variety of undesirable plants, including broadleaf weeds, such as smartweed, velvetleaf, redroot, pigweed, lambsquarters, latchweed, bedstraw, black medic, buckhorn plantain, annual purslane, black and nightshade; and grassy weeds such as crabgrass, annual bluegrass, creeping bentgrass, barnyard grass, orchard grass, woolly cup-grass, foxtails, shattercane, Kentucky bluegrass, Bermuda grass, perennial ryegrass and tall fescue. Thus, the dipeptides can be used as preemergence herbicides for application to established plots of desirable plants, including both monocotyledonous plants and dicotyledonous plants. Monocotyledonous crops include the grains; corn, sorghum, rice, oats, wheat, flax, rye, millet and the like. Dicotyledonous crops include fruits, fibers, herbs, vegetables, and legumes, including berry plants such as strawberries, blueberries and raspberries, soybeans, potatoes, spinach, cauliflower, tomatoes, tobacco, beans, beets, cotton, peas, squash, melons, canola, ornamental flowers and foliage and the like.

The application will be further described by reference to the following detailed examples.

EXAMPLE 1

Prior to filtration, liquid corn gluten was adjusted to about 14% solids with water and to pH 6.5 with dilute sodium hydroxide to yield 500 ml of the pH-adjusted gluten. Next, 0.07 ml THERMOLASE enzyme (an amylase available from Enzyme Development Corporation, New York, N.Y.) was added. The slurry was jet-cooked while adding steam at 160° C. for 3-4 minutes. To ensure complete liquification of the starch, 0.5 ml of CANALPHA 600 (an amylase from Biocon U.S., Inc., Lexington, Ky.) was added and the slurry held at 80° C. for one hour. The cooked gluten slurry was then cooled to 60° C., and its pH was adjusted to 4.6 with dilute hydrochloric acid. Another enzyme, 0.2 ml of ZYME-TEC 200, (a glucoamylase manufactured by Enzyme Technology, Inc., Ashland, Ohio) was added to the slurry and the slurry maintained at 60° C. for 13 hours.

The slurry was filtered through diatomaceous earth and the filter cake was washed with water. The filtrate and washings were discarded, the wet filter cake reslurried in water to about 12% solids and adjusted to pH 8.5 with Ca(OH)$_2$. Then, 0.2 ml of the protease enzyme, ALCALASE 2.4L (NOVO Laboratories, Danbury, Conn. was added while maintaining the reaction mixture at pH 8.5, 55° C. for 5 to 8 hours (or until such time that the pH remained constant). Afterwards, dilute phosphoric acid was added to adjust the pH to 6.5 to precipitate the calcium ion as calcium phosphate. The resulting suspension was then heated to 85° C. for 20 minutes to inactivate the enzyme. The solution was filtered and the cake washed with water, followed by combining the washings with the filtrate. The filter cake was discarded.

The clear, brown filtrate of corn gluten hydrolysate can be spray dried as is, or reduced by evaporation and then spray dried. The resulting dry product, corn gluten meal hydrolysate has the properties listed in Table II below.

TABLE II

| Appearance | Cream-tan powder |
| --- | --- |
| Dry substance, % | >90 |
| Solids recovery | >50 |
| Protein, % DB (% Kjeldahl nitrogen × 6.25) | >90 |
| pH (as 5% solution) | >6.5 |
| Water solubility (as 10% w/v solution) | soluble with slight haze |
| Ash, % DB | <5 |
| Odor | characteristic odor |

EXAMPLE 2

Corn gluten hydrolysate was prepared by a simplified procedure which also yields a water-soluble form of corn gluten of lower protein content.

As in Example 1, the liquid corn gluten is reconstituted in water, this time to about 10% solids. The slurry (500 ml) was then adjusted to pH 8.5 with a 10% slurry of calcium hydroxide. The protease enzyme, ALCALASE 2.4L (1.0% dry basis) was added and the solution stirred at 60° C. for 5 to 8 hours, or until such time that the pH remained constant at 8.5.

The material was then processed exactly as described in Example 1, to yield a corn gluten hydrolysate which has the properties shown in Table III, below:

TABLE III

| Appearance | cream-tan powder |
| --- | --- |
| Dry substance, % | >90 |
| Solids recovery | >50 |
| Protein, % DB (% Kjeldahl nitrogen × 6.25) | >70 |
| pH | 6.5 |
| Water solubility (10% solution) | soluble |
| Ash, % DB | <5 |
| Odor | characteristic odor |

EXAMPLE 3

The procedure of Example 2 was further simplified to yield a solubilized form of corn gluten of somewhat lower protein content by simply following the steps of Example 2, with the exception that the final filtration step was not carried out. After adjustment to a pH of 6.5 with phosphoric acid, the slurry was freeze-dried. The properties of the resulting product are shown on Table IV below:

TABLE IV

| Appearance | Cream-tan powder |
| --- | --- |
| Dry substance, % | >90 |
| Solids Recovery % | >95 |
| Protein, % DB (% Kjeldahl nitrogen × 6.25) | >50 |
| Water solubility (10% soln) | >50% of solids |
| pH | 6.5 |

EXAMPLE 4

The bioactive dipeptides were isolated and characterized employing the following procedures.

(1) Column Chromatography: an aqueous solution of the corn gluten hydrolysate of Example 1 (10% solids) was loaded on a Sephadex G-15 resin (Pharmacia) gel filtration column (28×998 mm)(cross-linked dextran, exclusion limit <1,500 daltons). Bioactive fractions of the eluate were identified with bioassays, then pooled and subjected to further purification steps. The bioassays were conducted in petri dishes using 10 perennial ryegrass (*Lolium perenne*) seeds placed on 1 layer of Whatman #1 filter paper of 38.5 cm$^2$ in area. The dishes were sealed with parafilm and placed in a controlled environmental chamber. The light intensity in the growth chamber was 70 μmol m$^{-2}$s$^{-1}$ at 25° C./15° C. day/night temperature with a 16 hr photoperiod. One ml of a given eluate fraction was applied to the filter paper in each petri dish. The study was conducted with seven replications for each eluate fraction.

(2) The bioactive fractions identified in step 1 were injected into a high performance liquid chromatograph (HPLC) equipped with a reverse phase (RP) C18 column (DYNA-MAX, 5μ, 10.0×250 mm) using a methanol in water gradient (0–5% methanol) for 10 minutes with a flow rate of 4 ml/min. The bioactive peak was isolated and subjected to amino acid analysis and peptide sequencing.

(3) Purified samples obtained from step 2 were derivatized with phenylisothiocyanate (PITC) to form phenylthiocarbamyl (PTC) peptides which were resolved using HPLC equipped with a narrow-bore (2.1×250 mm) C18-RP column (VYDAC) using 5% to 45% B in A in 35 min (A=0.1% TFA in $H_2O$; B=0.08% trifluoroacetic acid in $CH_3CN$) at a flow rate of 300 μl/min.

(4) The polypeptides were sequenced on a Biosystem 477A Protein Sequencer with a 120A PTH Amino Acid Analyzer. The isolated bioactive peak was resolved into 5 dipeptides: Gln-Gln, Ala-Asn, Ala-Gln, Gly-Ala and Ala-Ala.

EXAMPLE 5

Four synthetic dipeptides of the same structure as the dipeptides identified from the sample purified from the corn gluten hydrolysate were obtained from the Sigma Chemical Co., St. Louis, Mo. The fifth, Gln-Gln, was obtained from Bachem Bioscience Inc. The activity of each synthetically derived peptide was tested in seven replications on perennial ryegrass using the same bioassay technique described in Example 4 in the presence of increasing amounts of the dipeptides mixed with distilled water (Table V).

TABLE V

Root-Inhibiting Activity of the Five Identified Dipeptides on Perennial Ryegrass Seeds
Root Length of Perennial Ryegrass Seedlings Expressed as a Percentage of the Control (%),
Average of 2 Trials

| Dipeptides μg/cm$^2$* | Gln—Gln | Ala—Asn | Ala—Gln | Gly—Ala | Ala—Ala |
|---|---|---|---|---|---|
| 0 | 100 | 100 | 100 | 100 | 100 |
| 8 | 107 | 101 | 83** | 95 | 74** |
| 13 | 89 | 85 | 70 | 68 | 44 |
| 21 | 82 | 63 | 49 | 29 | 27** |
| 26 | 63 | 29 | 41 | 16 | 5 |
| 31 | 12 | 2 | 4 | 9 | 1** |
| 39 | 3* | 0 | 0 | 2 | 2 |
| 52 | 0 | 0 | 0 | 0 | 0 |

*Each dish contained a Whatman No. 1 filter paper measuring 38.5 cm$^2$ in area.
**Only one trial was performed.

All of the dipeptides except Gln-Gln reduced rooting of the perennial ryegrass at least 50% at the 26 μg/cm$^2$ rate. There was almost total inhibition of rooting at higher rates. The most effective dipeptides were Ala-Asn and Ala-Ala.

EXAMPLE 6

In a study designed to verify the bioactivity of the dipeptides on soil, Ala-Gln and Gly-Ala were applied to the surface of 56.3 cm$^2$ plastic pots filled with a Nicollet (fine, loamy, mixed mesic, Aquic Hapludol soil. The two dipeptides were applied at 0 to 3552 mg/dm$^2$. Data were collected 21 days after treatment on percentage survival of seedlings and on the mean length of roots in mm. The test specie was creeping bentgrass (*Agrostis palustris*). The results are shown on Table VI, below.

TABLE VI

PERCENTAGE (%) OF CREEPING BENTGRASS PLANTS SURVIVING 25 DAYS AFTER TREATMENT, AND MEAN ROOT LENGTH OF SEEDLINGS (mm)

| Dipeptide (mg/dm$^2$) | Ala—Gln | | Gly—Ala | |
|---|---|---|---|---|
| | -%- | -mm- | -%- | -mm- |
| 0 | 100 | 25 | 100 | 25 |
| 89 | 100 | 20 | 105 | 20 |
| 178 | 40 | 15 | 40 | 15 |
| 355 | 30 | 2 | 30 | 5 |
| 710 | 25 | 0 | 25 | 2 |
| 1066 | 5 | 0 | 25 | 2 |

TABLE VI-continued

PERCENTAGE (%) OF CREEPING BENTGRASS PLANTS SURVIVING 25 DAYS AFTER TREATMENT, AND MEAN ROOT LENGTH OF SEEDLINGS (mm)

| Dipeptide (mg/dm$^2$) | Ala—Gln | | Gly—Ala | |
|---|---|---|---|---|
| | -%- | -mm- | -%- | -mm- |
| 1776 | 0 | 0 | 0 | 0 |
| 3552 | 0 | 0 | 0 | 0 |

The data in Table VI indicate that Ala-Gln and Gly-Ala can completely inhibit the emergence and establishment of creeping bentgrass at concentrations of 1.8 g/dm$^2$ and above, and are partially effective at much lower concentrations.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for selectively inhibiting the growth of undesirable plants in a plot of soil comprising applying an amount of a dipeptide selected from the group consisting of Gln-Gln, Ala-Asn, Ala-Gln, Gly-Ala, Ala-Ala and mixtures thereof, to the plot of soil prior to the emergence of the undesirable plants, wherein said amount is effective to inhibit the growth of the undesirable plants by inhibiting their root development.

2. The method of claim 1 wherein the plot of soil also comprises desirable plants and the dipeptide is applied after the emergence of the desirable plants, at a level which does not inhibit the growth of the desirable plants.

3. The method of claim 1 further comprising planting desirable established plants in the plot of soil, which desirable plants are not inhibited in their growth by the amount of the dipeptide applied to said plot of soil.

4. The method of claim 3 further comprising applying an additional amount of said dipeptide to said plot of soil, so that the emergence of undesirable plants is inhibited while not inhibiting the growth of said desirable plants.

5. The method of claims 1, 2 or 3 wherein the dipeptide is applied in combination with a liquid carrier vehicle.

6. The method of claim 5 wherein the dipeptide is applied as an aqueous solution or dispersion.

7. The method of claims 1, 2 or 3 wherein the dipeptide is applied in combination with a solid carrier vehicle.

8. The method of claims 1, 2 or 3 wherein the dipeptide is applied to the soil plot at a concentration of about 0.25–5 g/dm$^2$.

9. The method of claims 1, 2 or 3 wherein the undesirable plants are grassy weeds.

10. The method of claims 1, 2 or 3 wherein the undesirable plants are broadleaf weeds.

11. The method of claims 1, 2 or 3 wherein the desirable plants are monocotyledonous.

12. The method of claim 11 wherein the desirable plants are turfgrasses.

13. The method of claims 2 or 3 wherein the desirable plants are dicotyledonous plants.

14. The method of claim 13 wherein the desirable plants are berry plants or ornamental flowers.

15. The method of claim 13 wherein the desirable plants are strawberry plants.

16. A preemergence herbicidal composition comprising an herbicidally effective amount of a dipeptide selected from the group consisting of Gln-Gln, Ala-Asn, Ala-Gln, Gly-Ala, Ala-Ala and mixtures thereof, in combination with a compatible carrier vehicle.

17. The composition of claim 16 wherein the carrier vehicle is a liquid.

18. The composition of claim 17 wherein the composition is an aqueous solution or dispersion of said peptide.

19. The composition of claim 16 wherein the carrier vehicle is a finely divided solid.

* * * * *